(12) United States Patent
Wang et al.

(10) Patent No.: US 8,404,688 B2
(45) Date of Patent: Mar. 26, 2013

(54) NITRONE COMPOUNDS, PROCESS OF PREPARATION THEREOF, AND USE THEREOF IN MEDICAMENT MANUFACTURE

(75) Inventors: Yuqiang Wang, Guangzhou (CN); Jie Jiang, Guangzhou (CN); Pei Yu, Guangzhou (CN); Yewei Sun, Guangzhou (CN); Linda Wang, Cupertino, CA (US); Zaijun Zhang, Guangzhou (CN)

(73) Assignee: Jinan University, Guangzhou (CN)

( * ) Notice: Subject to any disclaimer, the term of this patent is extended or adjusted under 35 U.S.C. 154(b) by 171 days.

(21) Appl. No.: 12/937,405

(22) PCT Filed: Apr. 16, 2009

(86) PCT No.: PCT/CN2009/071312
§ 371 (c)(1),
(2), (4) Date: Oct. 18, 2010

(87) PCT Pub. No.: WO2009/129726
PCT Pub. Date: Oct. 29, 2009

(65) Prior Publication Data
US 2011/0034485 A1  Feb. 10, 2011

(30) Foreign Application Priority Data
Apr. 25, 2008 (CN) .......................... 2008 1 0027706

(51) Int. Cl.
*A61K 31/4965* (2006.01)
(52) U.S. Cl. ..................................... 514/252.1; 544/336
(58) Field of Classification Search .................... 544/336
See application file for complete search history.

(56) References Cited

U.S. PATENT DOCUMENTS

2009/0318454 A1* 12/2009 Weiner et al. ................. 514/242

FOREIGN PATENT DOCUMENTS

| EP | 0967207 A1 | 12/1999 |
|---|---|---|
| WO | 99/20601 | 4/1999 |
| WO | 99/36420 | 7/1999 |
| WO | 00/32567 | 6/2000 |

OTHER PUBLICATIONS

Sun et al. Antioxidative and thrombolytic TMP nitrone for treatment of ischemic stroke. 2008. Bioorganic & Medicinal Chemistry, 16, 8868-8874.*
Kejian Li, A Systematic Review of Ligustrazine Injection for Acute Ischaemic Stroke, Lihsizhen Medicine and Materia Medica Research, vol. 17, No. 10, 1874-1875 (2006).
Jianxin Song et al., Mechanism of Ligustrazini against Thrombosis Chinese Medical Journal, 113( 2), 136-139 (2000).
Joen-Rong Shed et al., Mechanisms Involved in the Antiplatelet Activity of Tetramethylpyrazine in Human Platelet, Thrombosis Research, 88, 259-270 (1997).
Si-Yu Liu et al., Antiplatelet Structure-Activity Relationship of Tetramethylpyrazine, Life Sciences, vol. 55, No. 17, 1317-1326 (1994).
George Hsiao et al., Inhibitory Mechanisms of Tetramethylpyrazine in Middle Cerebral Artery Occlusion (MCAO)-Induced Focal Cerebral Ischemia in Rats, Planta Med., 72, 122-125 (2006).
Tsung-Kuei Kao, et al., Neuroprotection by Tetramethylpyrazine against Ischemic Brain Injury in Rats, Neurochemistry International, 48, 166-176 (2006).
Jin Xia Zhu et al., Activation of Apical CFTR and Basolateral Ca2+-Activated K+ Channels by Tetramethylpyrazine in Caco-2 Cell Line, European Journal of Pharmacology, 510, 187-195 (2005).

* cited by examiner

Primary Examiner — Brian McDowell
(74) Attorney, Agent, or Firm — Maschoff Brennan

(57) ABSTRACT

The present invention provides novel nitrones, their preparation and use. The novel compounds have the following formula: I The compounds of the present invention have strong antioxidative activity, and are thrombolytic. These compounds can be used to treat and/or prevent diseases caused by overproduction of free radicals and/or formation of thrombus.

3 Claims, 3 Drawing Sheets

NITRONE COMPOUNDS, PROCESS OF PREPARATION THEREOF, AND USE THEREOF IN MEDICAMENT MANUFACTURE

FIELD OF THE INVENTION

The present invention relates to novel nitrone compounds, their preparation and use in the manufacture of medicaments to treat and/or prevent neurological, inflammatory, metabolic, cardiovascular and cerebrovascular, neurodegenerative and aging-related disorders that result primarily from the overproduction of free radicals and/or thrombosis.

BACKGROUND OF THE INVENTION

Under normal conditions, the rate of reactive oxygen species (ROS) production does not exceed the capacity of the tissue to catabolize them. Under certain conditions, however, ROS levels are raised beyond the capacity of these protective mechanisms (e.g., irradiation, environmental factors, iron loading, etc.) or when these mechanisms are faulty (e.g., genetic defects), the ROS can cause cellular and tissue damage leading to a variety of diseases and even death. Proteins, lipids, and DNA are all substrates for ROS attack. It has been calculated that for every 100 tons of oxygen consumed two tons form ROS. For every $10^{12}$ oxygen molecules entering a cell each day 1/100 damages protein and 1/200 damages DNA. It is this damage to DNA, proteins, and lipids that makes the ROS so dangerous, especially when the body's natural defenses are compromised.

It is suggested that oxidative stress plays an important role in aging. The levels of some antioxidant enzymes such as superoxide dismutase (SOD) and antioxidants such as uric acid, beta-carotene and vitamin E have a positive correlation with the life-span of biological species. Namely, the level of these antioxidant enzymes and antioxidants decreases from human to chimpanzee to mouse (Culter, *Free Radicals in Biology*, vol. 4: p. 371, 1984). One hypothesis is that cells are damaged by free radicals and the damaged cells cannot function properly, and that the accumulation of damages to cells leads to aging (Culter, Id.). Another hypothesis is that free radicals cause cells to dysdifferentiate from their proper state of differentiation, and that this dysdifferentiation of cells leads to aging and all kinds of age-related diseases (Culter, Id.). It is suggested that free radicals cause aging and age-related diseases. Free radicals have been implicated in stroke, ischemia-reperfusion, cardiovascular diseases, carcinogenesis and neurological diseases, including Alzheimer's disease, Parkinson's disease, dementia and Hodgkin's disease.

Complications of atherosclerosis, such as myocardial infarction, stroke and peripheral vascular disease account for half of the deaths in the United States. Arteriosclerosis begins with an injury to the endothelial cells and is associated with the proliferation of muscle cells inside the arteries. In the process of atherosclerosis, blood becomes thick and platelets, oxidized low density lipoprotein (LDL, the major lipid in LDL is cholesterol esters) and other substances begin to adhere to the walls of the arteries causing the formation of plaque. The oxidation of LDL is caused by free radicals.

It was first recognized in 1969 (McCully, *Amer. J. Pathol.* 56:111, 1969), and only recently rediscovered, that high level of plasma homocysteine is associated with an increased rate of death due to coronary artery disease (Nygard et al., *N. Engl. J. Med.* 24: 337, 1997; Graham et al., *J. Am. Med. Assoc.* 277:1775, 1997). Homocysteine injures endothelial cells, thereby causing atherosclerosis through a number of mechanisms, including the generation of hydrogen peroxide ($H_2O_2$). It has been reported that homocysteine decreased the bioavailability of NO (not its production) and impaired the intracellular antioxidant enzymes, especially the glutathione peroxidases (Upchurch et al., *J. Biol. Chem.* 272: 17012, 1997). The key event in the process is generation and presence of free radicals. The increase of hydrogen peroxide can be a cause or a result. Homocysteine causes the production of free radicals including superoxide ($O_2 \cdot ^-$) which reacts with NO causing decreased bioavailability of NO and production of hydroxyl radical (.OH), or undergoes dismutation by SOD to produce hydrogen peroxide. Hydrogen peroxide is further converted to the reactive hydroxyl radical (.OH) through the Fenton reaction and the metal-catalyzed Haber-Weiss reaction. The free radicals produced as a result of these reactions will damage the antioxidant enzymes which prevents the detoxification of free radicals. It is clear that scavenging free radicals will prevent the toxic effects of LDL and homocysteine and results in the prevention of atherosclerosis.

Extensive research efforts, which include the use of antioxidant enzymes and antioxidants, have been made to counter the damaging effects caused by free radicals. Unfortunately, protein enzymes are too big to penetrate the cell wall and blood brain barrier. Antioxidants alone are not satisfactory for various reasons including the fact that they are consumed by free radicals and, thus, a large quantity is needed.

Several ROS exist. Diatomic molecular oxygen ($O_2$) readily reacts to form partially reduced species, which are generally short-lived and highly reactive and include the superoxide anion ($O_2 \cdot ^-$), hydrogen peroxide ($H_2O_2$), and hydroxyl radicals (.OH). The ROS are the byproducts of mitochondrial electron transport, various oxygen-utilizing enzyme systems, peroxisomes, and other processes associated with normal aerobic metabolism as well as lipid peroxidation. These damaging byproducts further react with each other or other chemicals to generate more toxic products. For example, hydrogen peroxide can be transformed to highly reactive hydroxyl radical (.OH) through the Fenton reaction and the metal catalyzed Haber-Weiss reaction:

$$Fe^{2+} + H_2O_2 \rightarrow Fe^{3+} + .OH + OH^-$$

$$.OH + OH^- \rightarrow O_2 \cdot ^- + H^+ \text{ (Fenton reaction)}$$

$$O_2 \cdot ^- + H_2O_2 \rightarrow .OH + OH^- + O_2 \text{ (}Fe^{3+}/Fe^{2+}\text{ catalyzed Haber-Weiss reaction)}$$

Superoxide ($O_2 \cdot ^-$) reacts with nitric oxide (NO) to form the toxic peroxynitrite (ONOO$^-$) which further decomposes to release the hydroxyl radical (.OH).

$$O_2 \cdot ^- + NO \rightarrow ONOO^- \rightarrow NO_2 \cdot + .OH$$

Human beings have a defense system against toxic byproducts of metabolism including various enzymes such as superoxide dismutase (SOD), catalases and peroxidases, and various antioxidants such as vitamins (e.g., vitamin A, beta-carotene, vitamin C and vitamin E), glutathione, uric acid and other phenolic compounds. SOD catalyzes the conversion of superoxide into hydrogen peroxide and oxygen.

$$2H^+ + O_2 \cdot ^- + O_2 \cdot ^- \rightarrow H_2O_2 + O_2 \text{ (catalyzed by SOD)}.$$

Hydrogen peroxide can be transformed by catalases and peroxidases to oxygen and water.

$$2H_2O_2 \rightarrow O_2 + H_2O \text{ (catalyzed by catalases and peroxidase)}$$

Despite the high efficiency of the defense system, some of these damaging species escape. The escaped reactive oxygen species and their products react with cellular DNA, protein and lipid resulting in DNA damage and peroxidation of membrane lipids. The deleterious results caused by reactive oxygen species are termed oxidative stress which affects normal gene expression, cell differentiation (Culter, *Free Radicals in Biology*, vol. 4, p. 371, 1984; Culter, *Ann. New York Acad. Sci.* 621: 1, 1991) and leads to cell death. Oxidative stress is now considered to be responsible for many health problems like cardiovascular and neurological diseases, cancer and other aging-related diseases as well as the human aging process.

Cholesterol plaques cause hardening of the arterial walls and narrowing of the inner channel (lumen) of the artery. Arteries that are narrowed by atherosclerosis cannot deliver enough blood to maintain normal function of the parts of the body they supply. For example, atherosclerosis of the arteries in the legs causes reduced blood flow to the legs. Reduced blood flow to the legs can lead to pain in the legs while walking or exercising, leg ulcers, or a delay in the healing of wounds to the legs. Atherosclerosis of the arteries that furnish blood to the brain can lead to vascular dementia or stroke.

Cerebrovascular disease is the third leading cause of death after heart disease and cancer in developed countries. Five percent of the population over 65 is affected by a stroke. In the United States, stroke afflicts more than 500,000 people every year (Digravio, G., *J. Am. Med. Assoc.* 296:2923, 2006). Seventy to eighty-five percent of stroke injuries are due to ischemic stroke, which has major morbidity and a 15~33% rate of mortality. Emerging treatments for acute cerebral ischemia include use of cytoprotective and thrombolytic agents (Phillips et al., *Prog. Cardiovasc Dis.*, 50: 264, 2008). While cytoprotective treatments attempt to prevent cell death during ischemia and reperfusion, thrombolytic treatment depends on the early use of clot-lysing agents and the restoration of blood flow. Despite intensive research efforts, stroke remains one of the most devastating diseases in medicine. One reason for the ineffectiveness of the current stroke therapy is that no drug currently used functions effectively as a thrombolytic and cytoprotective agent at the same time.

Reduced blood supply to the heart muscle from coronary atherosclerosis leads to coronary heart diseases, which include heart attacks, sudden unexpected death, chest pain (angina), abnormal heart rhythms, and heart failure due to weakening of the heart muscle.

Most heart attacks occur as a result of coronary artery disease (CAD). CAD is the buildup over time of plaque on the inner walls of the coronary arteries. Occasionally, a section of plaque can break open, causing a blood clot to form at the site. A heart attack occurs if the clot becomes large enough to cut off most or all of the blood flow through the artery. If blood flow is not restored within 20 to 40 minutes, irreversible death of the heart muscle will begin to occur. Muscle continues to die for six to eight hours at which time the heart attack usually is "complete." Treatment of heart attacks should include use of thrombolytic agents to dissolve the blood clot, following by the use of antioxidant to protect/salvage the damaged heart muscle cells.

SUMMARY OF THE INVENTION

The present invention provides compounds that can be used in the treatment and prevent of diseases that result from the overproduction of reactive oxygen species (ROS) and/or formation of blood clot. The compounds are of the following formula (I) or pharmaceutically acceptable salts thereof:

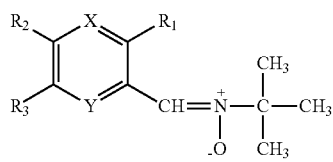

wherein:
$R_1$, $R_2$, and $R_3$ are independently H, OH, $NH_2$, COOH, alkyl, aryl, heteroaryl, ester, amide, or carbamate, and can be the same or different; and X and Y are independently C, N, O and S, but are not C at the same time.

In one preferred embodiment of the compounds of formula (I), $R_1$, $R_2$, and $R_3$ are independently H, OH, $NH_2$, COOH, alkyl, aryl, heteroaryl, ester, amide, or carbamate, and can be the same or different, and both X and Y are N.

In another preferred embodiment of the compounds of formula (I), $R_1$, $R_2$, and $R_3$ are independently alkyl, and can be the same or different, and both X and Y are N.

In yet another preferred embodiment of the compounds of formula (I), $R_1$, $R_2$, and $R_3$ are methyl, and both X and Y are N, and the compound has the following structure of formula (II):

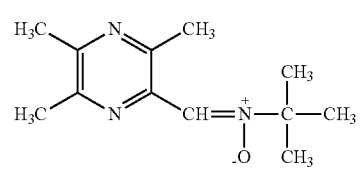

The present invention also provides a method of treating and/or preventing diseases that result from the overproduction of ROS and/or formation of blood clot. The method comprises administering to a patient an effective amount of a pharmaceutically acceptable carrier and one of more of the compounds of the following formula (I), or pharmaceutically acceptable salts thereof:

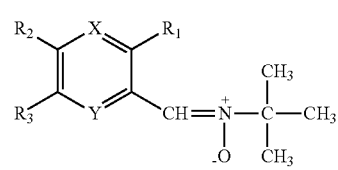

wherein:
$R_1$, $R_2$, and $R_3$ are independently H, OH, $NH_2$, COOH, alkyl, aryl, heteroaryl, ester, amide, or carbamate, and can be the same or different; and
X and Y are independently C, N, O and S, but are not C at the same time.

The present invention further provides a method of treating and/or preventing diseases that result from the overproduction of ROS and/or formation of blood clot. The method comprises administering to a patient an effective amount of a pharmaceutically acceptable carrier and the compound of formula (II), or pharmaceutically acceptable salts thereof:

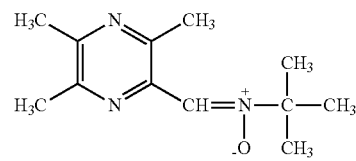

The present invention further features pharmaceutical compositions, comprising a pharmaceutically effective amount of the compounds of formula (I) or formula (II), which are suitable for the treatment or prevention of neurological or cardiovascular diseases, inflammatory disorders, or cancers, together with a pharmaceutically acceptable carrier.

The present invention further features processes for making the compounds of formula (I) of formula (II).

The present invention further provides a use of the compound of formula (I) or formula (II), or a pharmaceutical composition thereof in manufacture of a medicament for treatment or prevention of neurological or cardiovascular diseases, inflammatory disorders, or cancers.

The present invention further provides a use of the compound of formula (II) or a pharmaceutical composition thereof in manufacture of a medicament for treatment or prevention of neurological or cardiovascular diseases, inflammatory disorders, or cancers.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

DETAILED DESCRIPTION OF THE INVENTION

Figure 1:
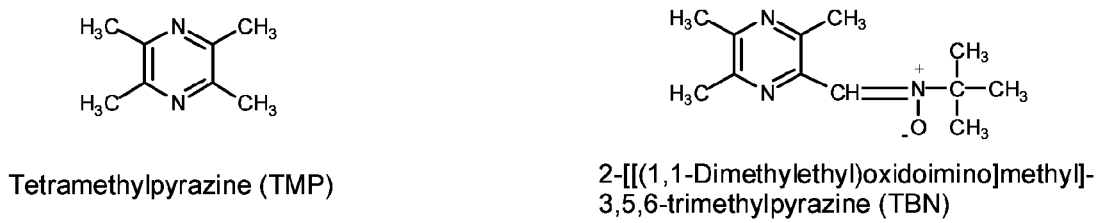
FIG. 1 shows the chemical structures of tetramethylpyrazine (TMP) and TBN.

The present invention provides compounds of the formula (I):

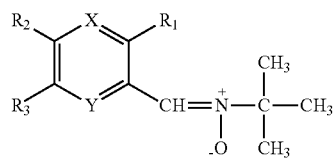

I wherein:
$R_1$, $R_2$, and $R_3$ are independently H, OH, $NH_2$, COOH, alkyl, aryl, heteroaryl, ester, amide, or carbamate, and can be the same or different; and
X and Y are independently C, N, O and S, but are not C at the same time.

In preferred embodiments of the compounds of formula (I), $R_1$, $R_2$, and $R_3$ are independently H, OH, $NH_2$, COOH, alkyl, aryl, heteroaryl, ester, amide, or carbamate, and can be the same or different, and both X and Y are N.

In another preferred embodiment of the compounds of formula (I), $R_1$, $R_2$, and $R_3$ are independently alkyl, and can be the same or different, and both X and Y are N.

In yet another preferred embodiment of the compounds of formula I, $R_1$, $R_2$, and $R_3$ are methyl, and both X and Y are N, and the compound has the following structure of formula (II):

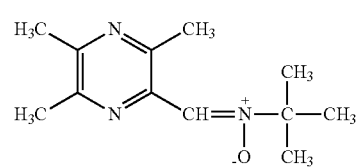

II

The compounds according to the present invention are effective for treating and/or preventing conditions associated with disorders resulting from overproduction of reactive oxygen species and/or formation of blood clot. The novel compounds according to the present invention include antioxidant with thrombolytic properties. As a result of the thrombolytic properties these compounds are useful in the prevention and treatment of cardiovascular, cerebrovascular and neurological disorders, inflammatory diseases and aging and age-related diseases.

The following definitions are set forth to illustrate and define the meaning and scope of the various terms used to describe the invention herein.

As used herein, the term "alkyl" refers to unsubstituted or substituted linear, branched or cyclic alkyl carbon chains of up to 15 carbon atoms. Such linear alkyl groups include, for example, methyl, ethyl, n-propyl, n-butyl, n-pentyl, n-hexyl, n-heptyl and n-octyl. Such branched alkyl groups include, for example, iso-propyl, sec-butyl, iso-butyl, tert-butyl and neopentyl. Such cyclic alkyl ("cycloalkyl") groups include, for example, cyclopropyl, cyclobutyl, cyclopentyl and cyclohexyl. The alkyl groups can be substituted with one or more substituents. Non-limiting examples of such substituents include $NH_2$, $NO_2$, O-alkyl, NH-alkyl, N(alkyl)$_2$, NHC(O)-alkyl, $ONO_2$, F, Cl, Br, I, OH, $OCF_3$, $OSO_2CH_3$, $CO_2H$, $CO_2$-alkyl, CN, aryl and heteroaryl. The term "alkyl" also refers to unsubstituted or substituted linear, branched or cyclic chains of up to 15 carbon atoms that contain at least one heteroatom (e.g., nitrogen, oxygen or sulfur) in the chain. Such linear alkyl groups include, for example, $CH_2CH_2OCH_3$, $CH_2CH_2N(CH_3)_2$ and $CH_2CH_2SCH_3$. Branched groups include, for example, $CH_2CH(OCH_3)CH_3$, $CH_2CH(N(CH_3)_2)CH_3$ and $CH_2CH(OCH_3)CH_3$. Such cyclic alkyl groups include, for example, $CH(CH_2CH_2)_2O$, $H(CH_2CH_2)_2NCH_3$, $CH(CH_2CH_2)_2S$, piperidino, piperidyl and piperazino. Such alkyl groups can be substituted with one or more substituents. Non-limiting examples of such substituents include $NH_2$, $NO_2$, O-alkyl, NH-alkyl, N(alkyl)$_2$, NHC(O)-alkyl, $ONO_2$, F, Cl, Br, I, OH, $OCF_3$, $OSO_2CH_3$, $CO_2H$, $CO_2$-alkyl, CN, aryl and heteroaryl. Further, the term also includes instances where a heteroatom has been oxidized, for example, to form an N-oxide, ketone or sulfone.

As used herein, the term "aryl" refers to an unsubstituted or substituted aromatic, carbocyclic group. Aryl groups are either single ring or multiple condensed ring compounds. A phenyl group, for example, is a single ring, aryl group. A naphthyl group exemplifies an aryl group with multiple condensed rings. Aryl groups can be substituted with one or more substituents. Non-limiting examples of such substituents include $NH_2$, $NO_2$, O-alkyl, NH-alkyl, $N(alkyl)_2$, NHC(O)-alkyl, $ONO_2$, F, Cl, Br, I, OH, $OCF_3$, $OSO_2CH_3$, $CO_2H$, $CO_2$-alkyl, CN, aryl and heteroaryl.

As used herein, the term "heteroaryl" refers to an unsubstituted or substituted aromatic mono- or poly-cyclic group containing at least one heteroatom within a ring, e.g., nitrogen, oxygen or sulfur. For example, typical heteroaryl groups with one or more nitrogen atoms include tetrazoyl, pyrrolyl, pyridyl (e.g., 4-pyridyl, 3-pyridyl, 2-pyridyl), pyridazinyl, indolyl, quinolyl (e.g., 2-quinolyl, 3-quinolyl), imidazolyl, isoquinolyl, pyrazolyl, pyrazinyl, pyrimidinyl, pyridonyl or pyridazinonyl; typical oxygen heteroaryl groups with an oxygen atom include 2-furyl, 3-furyl or benzofuranyl; typical sulfur heteroaryl groups are thienyl, and benzothienyl; typical mixed heteroatom heteroaryl groups include furazanyl, oxazolyl, isoxazolyl, thiazolyl, and phenothiazinyl. The heteroaryl groups can be substituted with one or more substituents. Non-limiting examples of such substituents include $NH_2$, $NO_2$, O-alkyl, NH-alkyl, $N(alkyl)_2$, NHC(O)-alkyl, $ONO_2$, F, Cl, Br, I, OH, $OCF_3$, $OSO_2CH_3$, $CO_2H$, $CO_2$-alkyl, CN, aryl and heteroaryl. Further, the term also includes instances where a heteroatom within the ring has been oxidized, for example, to form an N-oxide, ketone or sulfone.

As used herein, the term "pharmaceutically acceptable" refers to a lack of unacceptable toxicity in a compound, such as a salt or excipient. Pharmaceutically acceptable salts include inorganic anions such as chloride, bromide, iodide, sulfate, sulfite, nitrate, nitrite, phosphate, and the like, and organic anions such as acetate, malonate, pyruvate, propionate, cinnamate, tosylate, citrate, and the like. Pharmaceutically acceptable excipients are described below, and, at length by E. W. Martin, in Remington's Pharmaceutical Sciences, Mack Publishing Company (1995), Philadelphia, Pa., 19th ed.

There are many reports on the treatment of stroke with traditional Chinese medicine, and among the widely used are Dan shen and Chuan xiong (tetramethylpyrazine, or TMP). They have been reported to have beneficial effects in treatment of stroke and are safe (Li Kejian, Lishizhen Medicine and Materia Medica Research 17:1874, 2006). TMP has numerous pharmaceutical effects including the following:

(1) TMP has significant anticogulation activity. TMP inhibits the expression of LPS-induced PAI-1 protein and its mRNA in endodermis cells (Song et al., *Chinese Medical J.* 113:136, 2000). TMP at low dose of inhibits the disassociation of inositol phospholipid and the formation of TXA2, and TMP at high dose inhibits platelet aggregation via the binding of glycoprotein IIb/IIIa (Sheu et al., *Thromb Res.* 88:259, 1997).

(2) TMP has thrombolytic activity. TMP showed thrombolytic activity in both the rat arterio- and phlebo-thrombosis models (Liu and Sylvester, *Thromb Res.* 58:129, 1990). TMP inhibits platelet activity, $Ca^{2+}$ inflow, and phosphodiesterase activity, and increases the level of cAMP (Liu and Sylvester, *Thromb Res.* 75:51, 1994). TMP decreases the death rate of ADP-induced acute pulmonary embolism; TMP given by intravenous injection significantly prolonged the bleeding time of rat arterial experiment by 1.5 times, which demonstrates its anti-aggregative effects (Sheu et al., *Thromb Res.* 88:259, 1997).

(3) TMP significantly protects neuronal cells (Hsiao et al., *Planta Med.* 72:411-417, 2006; Kao et al., *Neurochem Int.* 48:166, 2006). TMP significantly improves MCAo-induced rat brain ischemia damage, and diminishes the free radical produced by human neutrophile granulocyte. TMP can regulate the expression of Bcl-2 and Bax leading to reduced neuronal apoptosis.

(4) TMP is a $Ca^{2+}$ channel blocker, and opens the potassium channels resulting in the production of free radicals. TMP increases the activity of superoxide dismutase (SOD), and inhibit lipid peroxidation and inflammatory reaction (Zhu et al., *Eur J Pharmacol.* 510:187, 2005).

In summary, the long history of clinical use of TMP demonstrates that TMP has both the thrombolytic and antioxidant activity.

Nitrones and nitroxides are cell permeable and stable free radicals. Nitrone reacts with free radicals to form nitroxide which acts as superoxide dismutase and which mimics and catalyzes the dismutation of superoxide anion (Samuni et al., *J. Biol. Chem.* 263: 17921, 1988; Krishna et al, *J. Biol. Chem.* 271: 26018, 1996; Krishna et al, *J. Biol. Chem.* 271: 26026, 1996) and stimulates the catalase-like activity of hemeproteins (Krishna et al, *J. Biol. Chem.* 271: 26026, 1996) resulting in protection of cells from free radical mediated damage. One additional advantage of nitroxide over other antioxidants is that its concentration remains the same before and after the reaction because it acts as a catalyst. For example, phenyl-tert-butyl nitrone (PBN) reacts with free radicals to form nitroxide:

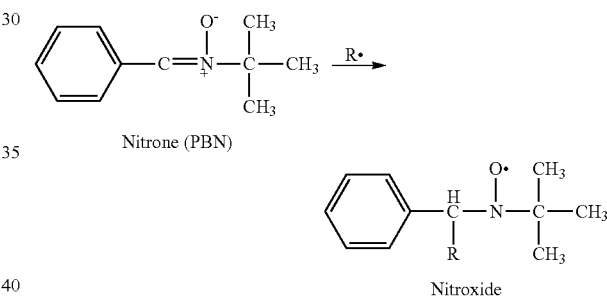

Nitroxide removes free radicals by reacting with free radicals directly or by oxidizing the reduced metals thereby inhibiting the Fenton and the metal-catalyzed Haber-Weiss reactions (Mohsen et al., *Mol. Cellul. Biochem.* 145:103, 1995). For example, 2,2,6,6-tetramethylpiperidine-1-oxyl (TEMPOL) removes superoxide ($O_2.^-$) in the following manner:

1.

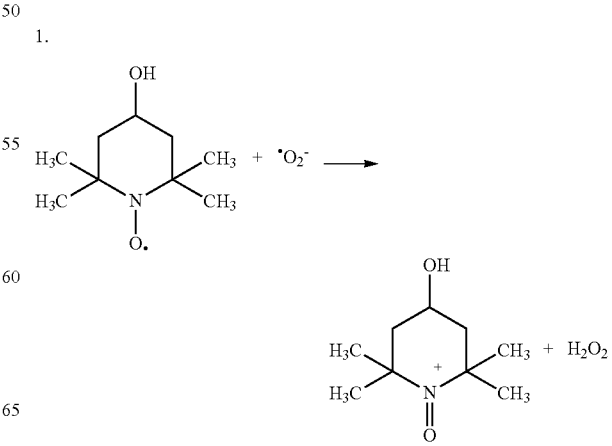

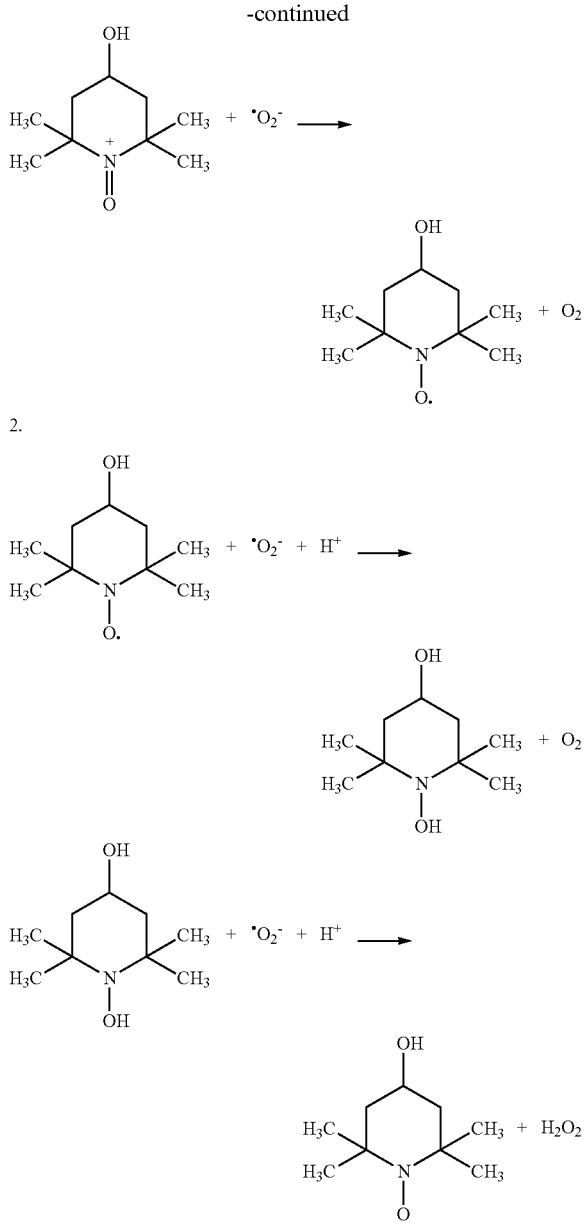

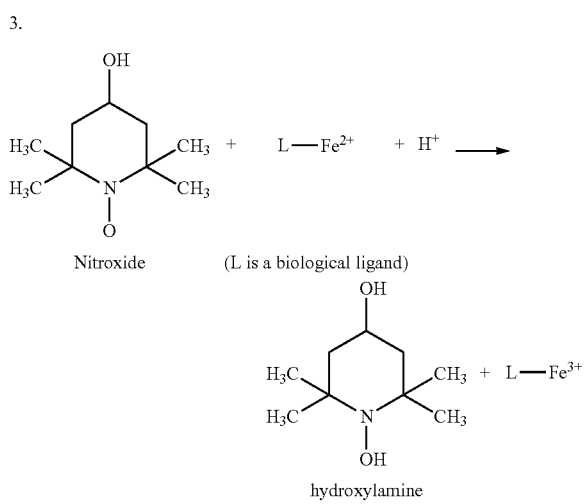

The terminal products of the reaction of nitrone with free radicals include hydroxylamine derivatives, aldehydes and amines. These products are much less damaging to cells than free radicals (Chamulitrat et al., *J. Biol. Chem.* 268:11520, 1993; Janzen et al., *Free Rad. Biol. Med.* 12:169, 1992; Kotake and Janzen, *J. Am. Chem. Soc.* 113:948, 1991). Daily intraperitoneal injection of PBN to sensescence accelerated mouse resulted in a 33% increase of life span (Edamatsu et al., *Biochem. Biophys. Res. Commun.* 211:847, 1995). When 24-month old rats were intraperitoneally injected with PBN at a dose of 32 mg/kg daily for 9.5 months, lipid peroxidation within two brain areas important for cognitive function, the neocortex and the globus pallidus, were reduced and the cognitive performance of the aged rats were improved. More impressively, at 32 months into the study, 7 of 11 PBN-treated rats were still alive (Sack et al., *Neurosci. Lett.* 205:181, 1996).

In another experiment, the nitroxide, 4-hydroxy-2,2,6,6-tetramethylpiperidine-1-oxyl alleviated heat hyperalgesia in rats with an experimental painful peripheral neuropathy (Tal, *Neuroreport* 7:13183, 1996). In isolated rat heart, nitroxide strongly protected against reperfusion injury by preventing the formation of hydroxyl radical (.OH) and not by decreasing heart rate or by direct suppression of arrhythmia (Gelvan et al., *Proc. Natl. Acad. Sci.* 88:4680 1991). Nitroxide afforded full protection of cardiomycytes of rats in culture in millimolar concentration without toxic side-effects from the toxicity of hydrogen peroxide (Mohsen et al., *Mol. Cellul. Biochem.* 145:103, 1995).

Ley et al (J. Pharmacol and Expert. Thera. 313:1090-1100, 2005; Brain Res. 1180: 101-110, 2007) reported that stilbazulenyl nitrone (STAZN) was highly neuroprotective in rodent models of cerebral ischemia and trauma. Physiologically regulated rats received a 2-h middle cerebral artery occlusion by intraluminal suture and were treated with either STAZN or dimethyl sulfoxide vehicle. STAZN improved neurological deficits compared with vehicle controls and STAZN confered enduring ischemic neuroprotection.

Another nitrone, disodium 4-[(tert-butylimino)methyl] benzene-1,3-disulfonate N-oxide (NXY-059) was shown to be effective for treatment of stroke. When male Wistar rats were subjected to 2 hour of MCA occlusion, followed by NXY-059 given 1 hour after recirculation, NXY-059 significantly reduced infarct volume at both 48 hours and 7 days (Kuroda et al., J. Cereb. Blood Flow Metab. 19, 778-787, 1999). Marshall et al (Stroke 32, 190-198, 2001) reported that NXY-059 treatment of monkeys suffering from permanent occlusion of the right middle cerebral reduced the overall amount of brain damage by >50% of saline-treated control monkeys.

These data demonstrated the usefulness of free radical-trapping nitrones and nitroxides as therapeutic agents for human diseases or preventive agents for aging.

The novel compounds according to the present invention include a TMP nitrone derivative (formula (I)) and TMP nitroxide derivatives (formulas (II) and (III)). The TMP nitrones and nitroxides of formulas (I), (II) and (III) are antioxidants with thrombolytic properties, which, on one hand, scavenge free radicals including superoxide ($O_2.^-$), peroxynitrite ($ONOO^-$) and hydroxyl radical (.OH) in human blood and tissues, and on the other hand, dissolve the blood clot in blood vessels. As a result, they may be useful in the prevention and treatment of diseases caused by overproduction of free radicals and/or formation of blood clot. These diseases include, but not limit to neurological diseases such as hypoxic-ischemic brain injury, stroke, trauma, Alzheimer's disease, epilepsy, Parkinson's disease, Huntington's disease, amyotrophic lateral sclerosis, AIDS dementia, multiple sclerosis, chronic pain, priapism, cystic fibrosis, schizophrenia, depression, premenstrual syndrome, anxiety, addiction and migraine; cardiovascular diseases such as cardiopulmonary bypass, ischemic/reperfusion injury, ischemic/reperfusion, toxic shock syndrome, adult respiratory distress syndrome, cachexia, myocarditis, atherosclerosis, coronary heart disease and heart attack; inflammatory diseases such as inflammatory bowel disease, diabetes, rheumatoid arthritis, asthma, cirrhosis, allograft rejection, encephalomyelitis, meningitis, pancreatitis, peritonitis, vasculitis, lymphocytic choriomeningitis, glomerulonephritis, systemic lupus erythematosis, gastrointestinal motility disorders, obesity, hyperphagia, hepatitis and renal failure; ophthalmologic diseases such as diabetic retinopathy, uveitis, glaucoma, blepharitis, chalazion, allergic eye disease, corneal ulcer, keratitis, cataract, age-related macular degeneration and optic neuritis. These novel agents may also be used to prevent/treat cancers such as neuroblastoma, and other age-related diseases.

The TMP nitrone and nitroxide compounds according to the present invention, and derivatives thereof, can be administered to a patient in the form of a pharmaceutically acceptable salt or in a pharmaceutical composition. A compound that is administered in a pharmaceutical composition is mixed with a suitable carrier or excipient such that a therapeutically effective amount is present. The term "therapeutically effective amount" refers to an amount of the compounds of the TMP nitrone or nitroxide derivative that is necessary to achieve a desired endpoint (e.g., preventing the overproduction of free radicals, decreasing cell damage as the result of a stroke, heart attack or inflammatory diseases, etc.).

A variety of preparations can be used to formulate pharmaceutical compositions containing the TMP nitrone or nitroxide derivatives, including solid, semi solid, liquid and gaseous forms (*Remington's Pharmaceutical Sciences*, Mack Publishing Company (1995), Philadelphia, Pa., 19$^{th}$ ed). Tablets, pills, granules, dragees, gels, slurries, ointments, solutions, suppositories, injections, inhalants and aerosols are examples of such formulations. The formulations can be administered in either a local or systemic manner or in a depot or sustained release fashion. Administration of the composition can be performed in a variety of ways. Among others, oral, buccal, rectal, parenteral, intraperitoneal, intradermal, transdermal and intratracheal means can be used.

Where the TMP nitrone or nitroxide compounds or their derivatives are given by injection, they can be formulated by dissolving, suspending or emulsifying it in an aqueous or nonaqueous solvent. Vegetable or similar oils, synthetic aliphatic acid glycerides, esters of higher aliphatic acids and proylene glycol are examples of nonaqueous solvents. The compound is preferably formulated in aqueous solutions such as Hank's solution, Ringer's solution or physiological saline buffer.

Where the TMP nitrone or nitroxide compounds or their derivatives are given orally, they can be formulated through combination with pharmaceutically acceptable carriers that are well known in the art. The carriers enable the compound to be formulated, for example, as a tablet, pill, suspension, liquid or gel for oral ingestion by the patient. Oral use formulations can be obtained in a variety of ways, including mixing the compound with a solid excipient, optionally grinding the resulting mixture, adding suitable auxiliaries and processing the granule mixture. The following list includes examples of excipients that can be used in an oral formulation: sugars such as lactose, sucrose, mannitol or sorbitol; cellulose preparations such as maize starch, wheat starch, potato starch, gelatin, gum tragacanth, methyl cellulose, hydroxyproylmethylcellulose, sodium carboxymethylcellulose and polyvinylpyrrolidone (PVP).

The TMP nitrone or nitroxide compounds or their derivatives according to the present invention can also be delivered in an aerosol spray preparation from a pressurized pack and a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Pharmaceutical compositions according to the present invention contain a therapeutically effective amount of the TMP nitrone or nitroxide compound or its derivative. The amount of the compound will depend on the patient being treated. The patient's weight, severity of illness, manner of administration and judgment of the prescribing physician should be taken into account in deciding the proper amount. The determination of a therapeutically effective amount of a TMP nitrone or nitroxide compound or its derivative is well within the capabilities of one with skill in the art.

Although a therapeutically effective amount of a TMP nitrone or nitroxide compound or its derivative will vary according to the patient being treated, suitable doses will typically be in the range between about 10 mg and 10 g of the compound.

In some cases, doses exceeding the specified range are needed, and these are explicit for physicians. Necessarily, physicians will know when and how to suspend, regulate or terminate therapy according to the response of particular patients.

The present invention is further illustrated by referring to the following examples, but these examples are not intended to further restrict the present invention. Obviously, those skilled in the art could modify the materials and methods without departing from the purpose and spirit of the present invention. The efficiency of the compound of the present invention can be detected in vivo and animal models according to the following measurements.

EXAMPLES

The following examples are intended for illustration only and are not intended to restrict the scope of the present invention in any way.

Example 1

Figure 2:
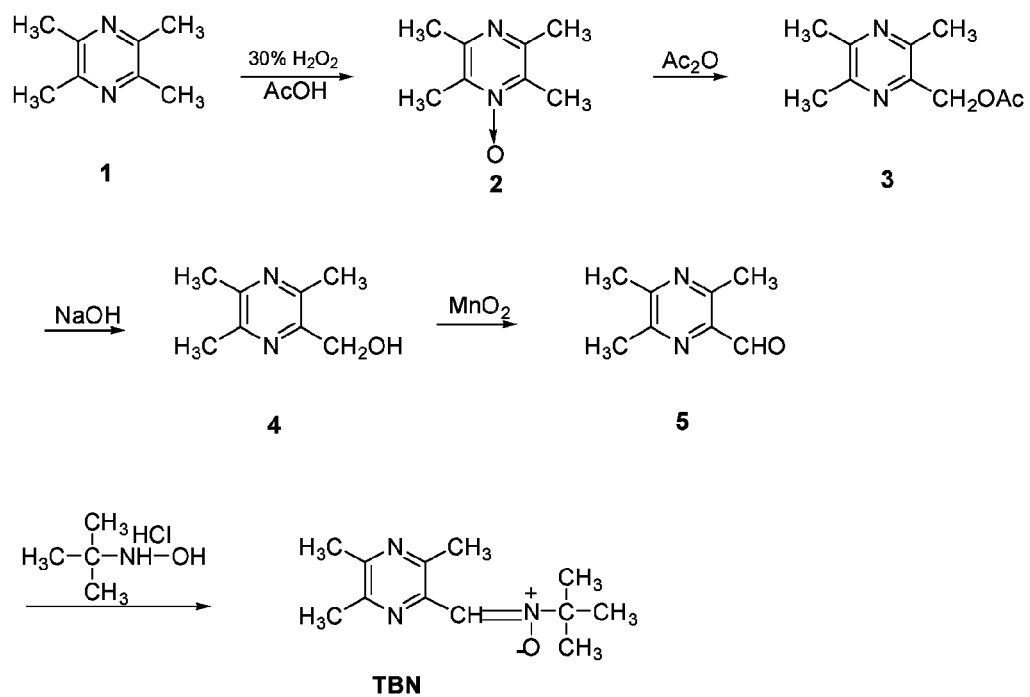
FIG. 2 is a scheme of an exemplary synthesis of TBN.

Synthesis of TBN (FIG. 2)

2-[[(1,1-Dimethylethyl)oxidoimino]methyl]-3,5,6-trimethylpyrazine (TBN). To aldehyde 5 (1.9 g, 0.013 mol) in methanol (200 mL) was added tert-butylhydroxylamine (1 g, 0.011 mol), and the solution was refluxed for 2 h. Another portion of tert-butyl hydroxylamine (1 g, 0.011 mol) was then added, and the solution refluxed until aldehyde 5 was completely reacted. Solvent was removed in vacuo, and the product was extracted. The solution was dried with $Na_2SO_4$, and solvent removed in vacuo. The product was purified by column chromatography, eluting with ethyl acetate/petroleum ether (1/1, v/v), to produce TBN as a light yellow solid (1.1 g, 38% yield), mp: 68-70° C. $^1$H NMR ($CDCl_3$, ppm): 7.82 (s, 1H), 2.47 (s, 3H), 2.50 (s, 3H), 2.52 (s, 3H), 1.63 (s, 9H). ESI-MS: 222 [M+H]$^+$, 244 [M+Na]$^+$. Anal. ($C_{12}H_{19}N_3O$) C, H, N.

Example 2

Figure 3:
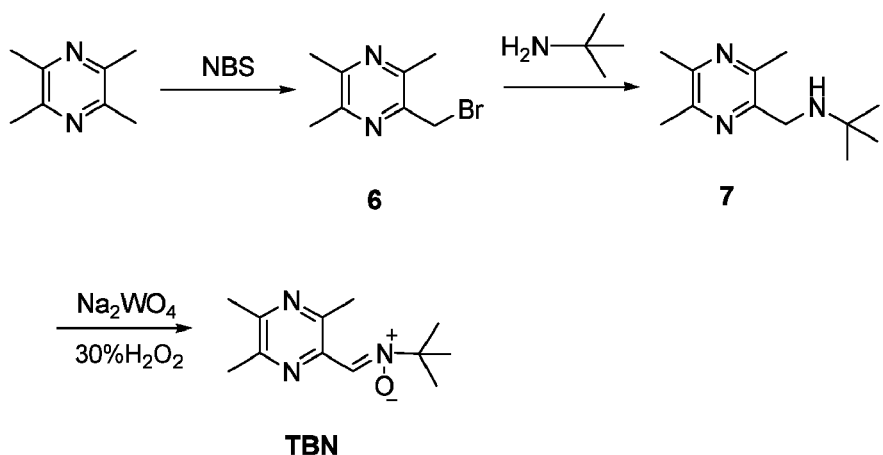
FIG. 3 is a scheme of another exemplary synthesis of TBN.

Synthesis of TBN (FIG. 3)

To compound 7 (1.0 g, 0.005 mol) in methanol (100 mL) was added $Na_2WO_4 \cdot 2H_2O$ (0.4 g) and 30% $H_2O_2$ (2.5 mL), and the reaction mixture was stirred at room temperature for 2 h. The product was filtered, and solvent removed in vacuo. To the residue was added saturated $Na_2S_2O_3$ solution (8 mL). The product was extracted with ethyl acetate (25 mL×3), and the solution was dried with $Na_2SO_4$. Solvent was removed in vacuo, and the product was purified by column chromatography, eluting with ethyl acetate/petroleum ether (1/1, v/v), to produce TBN as a light yellow solid (0.4 g, 36% yield).

Example 3

Protection of Neuronal Cells from Oxidative Damage by TBN

Cortical neurons ($9 \times 10^4$ cells/well) were placed into 96-well cell culture plates, and were incubated at 37° C. for 24 h under 5% $CO_2$. The medium was changed, and the cells were incubated for another 12 h. Drugs at different concentrations were added, and the cells were incubated at 37° C. for 30 min. Hydrogen peroxide were then added, and the cells were incubated for 24 h at 37° C. for 24 h under 5% $CO_2$. A solution of 3-(4,5-dimethylthiazol-2-ly)-2,5-diphenyl-tetrazoliun bromide (MTT) was added, and the cells were incubated for another 4 h before DMSO was added. After the crystals were completely dissolved (30 min), the absorbance was read at 570 nm with a spectrophotometer (Bio-Rad Model 680, Japan). The results were expressed as the percentage of the control (saline group).

Figure 4:
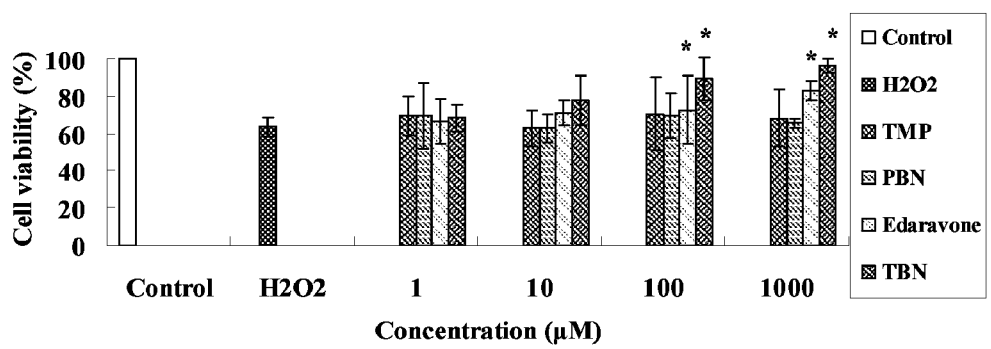
FIG. 4 is a diagram illustrating protection of neuronal cells from oxidative damage by TBN, where the data were expressed as the mean±S.E.M. of three independent experiments, and were processed statistically by a single-tail student's t-test, and *$P<0.05$ is compared to $H_2O_2$ group.

As shown in FIG. 4, TBN is more effective than either TMP or PBN in protecting cortical neuronal cells from $H_2O_2$-induced damage. TBN was approximately 10-fold more effective than Eda in protecting cortical neuronal cells from $H_2O_2$-induced damage.

Example 4

Protection of Neuronal Cells from Excitotoxicitic Damage by TBN

Figure 5:
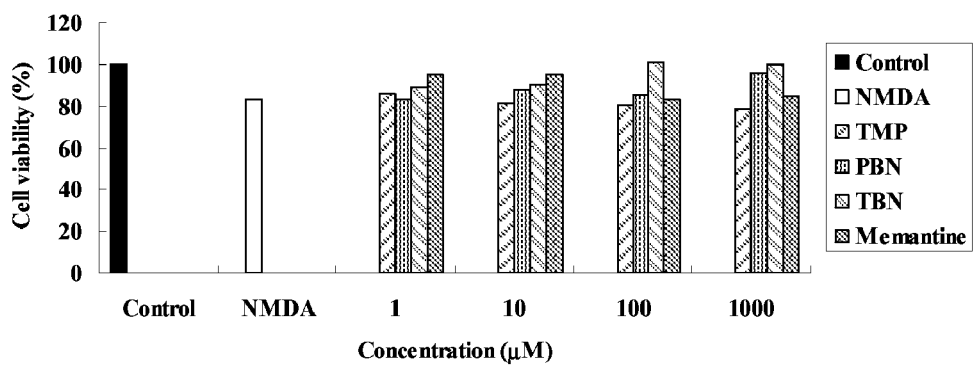
FIG. 5 is a diagram illustrating protection of neuronal cells from excitotoxicitic damage by TBN.

Cortical neurons ($9 \times 10^4$ cells/well) were placed into 96-well cell culture plates, and were incubated at 37° C. for 24 h under 5% $CO_2$. The medium was changed, and the cells were incubated for another 12 h. Drugs at different concentrations 1000 µM, 100 µM, 10 µM, 1 µM) were added, and the cells were incubated at 37° C. for 30 min. NMDA (15 µL) was then added (final concentration of NMDA is 100 µM), and the cells were incubated for 24 h at 37° C. for 24 h under 5% $CO_2$. As shown in FIG. 5, TBN significantly protected the neuronal cells from NMDA toxicity.

Example 5

Protection of Stroke by TBN in MCAo Rats

Female Sprague-Dawley rats (210-240 g) were anesthetized with 10% chloral hydrate (400 mg/kg) i.p. The right common carotid artery (CCA) was carefully exposed. The occipital branch of the external carotid artery (ECA) was coagulated and the internal carotid artery (ICA) was isolated. A poly-L-lysine-coated nylon suture (0.32 mm in diameter) was inserted into the ECA and advanced retrogradely until the bifurcation of the CCA from where it was advanced a distance of approximately 18-20 mm into the ICA to occlude the MCA. A ligature was tied around the ICA, the incisions were closed, and the animal was extubated.

TMP (50 mg/kg), TBN (80 mg/kg), PBN (65 mg/kg), Eda (62 mg/kg) and saline were administered i.p. 1 h after MAC occlusion, respectively. After 2 h of MCA occlusion, the suture was withdrawn to allow reperfusion. After 24 h of reperfusion, the animals were re-anesthetized with 10% chloral hydrate (400 mg/kg) i.p., and were then decapitated. The brain was quickly removed, rinsed with PBS, and stored in a refrigerator at −20° C. until it was frozen. The brain was sliced with a blade at every 2-mm from the frontal pole, and the slices were stained with 2,3,5-triphenyltetrazolium chloride (TTC, 0.5% in normal saline) for 30 min at 37° C. Electronic images of the sections were made with a high-resolution camera (Sony X700, Japan). The area of infarction was quantified by the Osiris 4 software, and the results were expressed as the percentage of the total brain section area.

Figure 6:
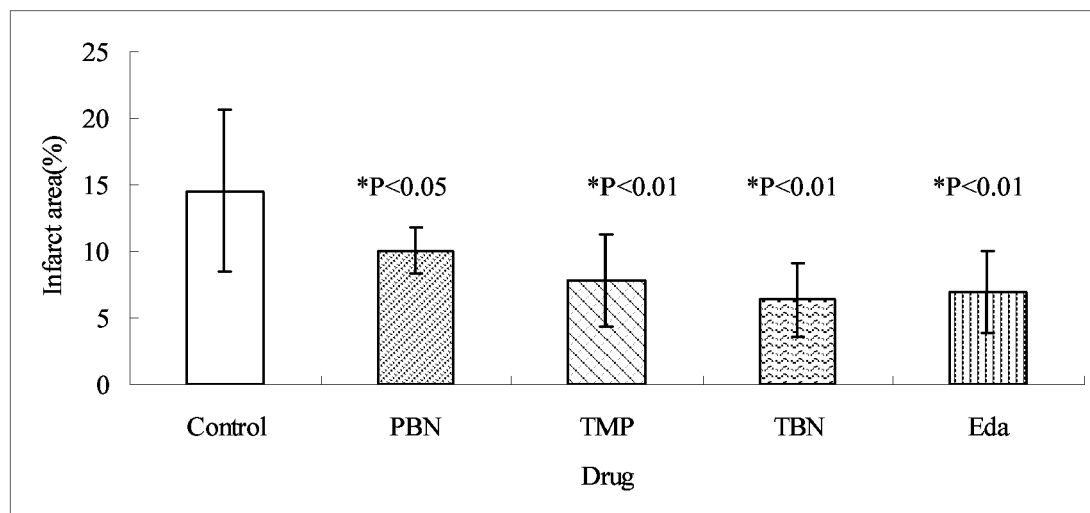
FIG. 6 is a diagram illustrating protection of stroke by TBN in MCAo rats, where rats were subjected to 2 h ischemia followed by 24 h of reperfusion, all drugs were in equal molar doses, and the data were processed statistically by a single-tail student's t-test, and it is noted that the mark "*" indicates data compared to the control.

As shown in FIG. 6, TBN had significant protective effects in the MCAo rat stroke model

Example 6

Thrombolytic Activity in Rats

Sprague-Dawley rats (180-210 g) were anesthetized with 10% chloral hydrate (400 mg/kg) i.p. The inferior vena cava was isolated and a tight ligature was applied below the left renal vein branch. The abdomen was then closed. Drugs were administered 2 h after ligation i.v. via the dorsal tail vein. The abdomen was reopened after 1 h of ligation. The thrombus was removed and dried at 50° C. for 24 h. The dried thrombus was weighted.

Figure 7:
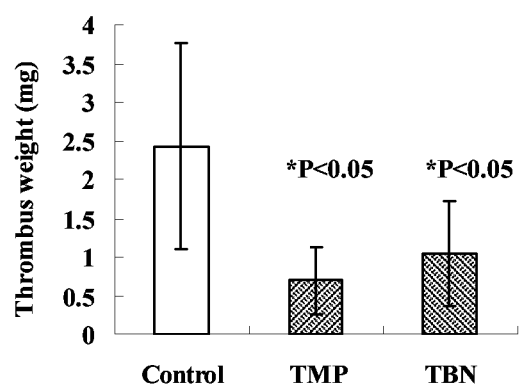
FIG. 7 is a diagram illustrating thrombolytic activity in rats, where the drug dose is TMP (2 mg/kg) and TBN (3.25 mg/kg), and the molar doses of TMP and TBN were the same. Further, the data were processed statistically by a single-tail student's t-test, and it is noted that the mark "*" indicates data compared to the control.

As shown in FIG. 7, TBN had significant thrombolytic activity in this rat model

The scientific publications, patents or patent applications cited in the various sections of this document are incorporated herein by reference for all purposes.

From the foregoing detailed description of the specific embodiments of the invention, it is shown that the novel compounds of this invention can be used as a unique method of treating or preventing disorders resulting from overproduction of free radicals, such as neurological, cardiovascular diseases, inflammatory disorders and/or cancers.

Although particular embodiments have been herein described in detail, the above description has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. A compound of the following formula (I) or a pharmaceutically acceptable salt thereof:

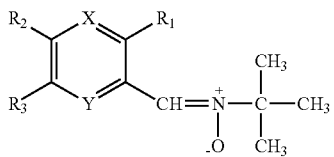

wherein:

R1, R2, and R3 are independently or alkyl, wherein the R1, R2, and R3 can be the same or different with the proviso that all R1, R2, and R3 cannot be H at the same time; and both X and Y are N.

2. The compound according to claim 1, wherein R1, R2, and R3 are methyl, and the compound has the following structure of formula (II):

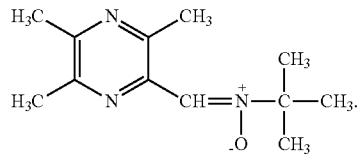

3. A pharmaceutical composition comprising a pharmaceutically effective amount of a compound according to claim 1 and a pharmaceutically acceptable carrier.

* * * * *

UNITED STATES PATENT AND TRADEMARK OFFICE
CERTIFICATE OF CORRECTION

PATENT NO. : 8,404,688 B2  
APPLICATION NO. : 12/937405  
DATED : March 26, 2013  
INVENTOR(S) : Wang et al.

Page 1 of 1

It is certified that error appears in the above-identified patent and that said Letters Patent is hereby corrected as shown below:

On the Title Page, Item (56), under "OTHER PUBLICATIONS", in Column 2, Line 9, delete "Shed et al.," and insert -- Sheu et al., --, therefor.

In the Claims

In Column 15, Line 15, in Claim 1, delete "independently or alkyl," and insert -- independently H or alkyl, --, therefor.

Signed and Sealed this  
Twenty-third Day of July, 2013

Teresa Stanek Rea  
*Acting Director of the United States Patent and Trademark Office*